| United States Patent [19] | [11] 4,014,999 |
| Mallory et al. | [45] Mar. 29, 1977 |

[54] HALO-STEROIDAL THIOKETALS FOR TREATING INFLAMMATION

[75] Inventors: Robert A. Mallory; Joseph A. Settepani, both of Somerville, N.J.

[73] Assignee: Ortho Pharmaceutical Corporation, Raritan, N.J.

[22] Filed: Mar. 2, 1976

[21] Appl. No.: 663,174

Related U.S. Application Data

[62] Division of Ser. No. 463,707, April 24, 1974, Pat. No. 3,970,646.

[52] U.S. Cl. .............................................. 424/241
[51] Int. Cl.$^2$ ......................................... A61K 31/58
[58] Field of Search .................................... 424/241

Primary Examiner—Stanley J. Friedman
Attorney, Agent, or Firm—Benjamin F. Lambert

[57] ABSTRACT

Halo steroidal thioketals having a 4-5-membered mono- or dithioketal at the 3-position and a halogen at the 6 and 9 positions are described. The halo thioketals are useful as anti-inflammatory agents.

10 Claims, No Drawings

HALO-STEROIDAL THIOKETALS FOR TREATING INFLAMMATION

This is a division of application Ser. No. 463,707, filed Apr. 24, 1974, now U.S. Pat. No. 3,970,646.

The present invention relates to a group of corticosteroid derivatives and more specifically to 6α, 9-dihalo-11β, 16α, 17,21-tetrahydroxypregna-1,4-diene-3,20-dione-16, 17-acetonide-3-alkylenethioketals and their 21 esters. The compounds of the present invention can be represented by the following structural formula:

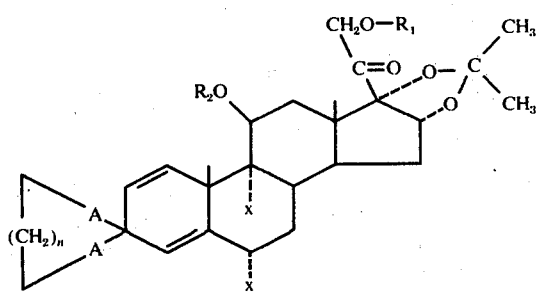

wherein $R_1$ is hydrogen, lower acyl having 2–5 carbon atoms such as, for example, acetyl, propionyl, butyryl or valeryl, tetrahydropyranyl, or lower alkyl having 1–5 carbon atoms such as, for example, methyl, ethyl, propyl and the like; $R_2$ is hydrogen or lower acyl having 2–5 carbon atoms; A is oxygen or sulfur, provided that at least one of A is sulfur; $x$ is fluoro, chloro, or bromo, and $n$ is an integer from 0–3.

Preferred among the compounds of the present invention are these compounds of the formula

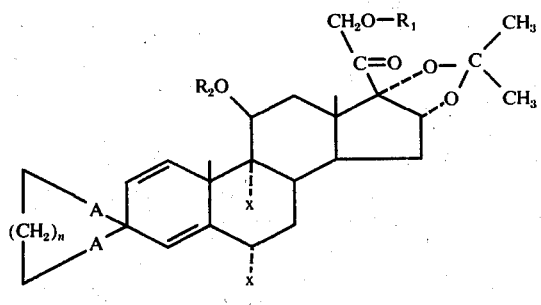

wherein $R_1$ is hydrogen, lower acyl having 2–5 carbon atoms, or tetrahydropyranyl; $R_2$ is hydrogen or lower acyl having 2–5 carbon atoms; A is oxygen or sulfur, provided that at least one of A is sulfur; $x$ is fluoro, and $n$ is an integer from 0–3.

The corticosteroid derivatives of the present invention can be prepared by reacting an appropriately substituted starting material such as 6α,9-difluoro-11β,16α,17,21-tetrahydroxypregna-1,4-diene-3,20-dione-16,17-acetonide with an alkane thiol such as, for example, 2-mercaptoethanol, ethanedithiol, propanedithiol, 2-mercaptopropanol, butanedithiol and the like in a suitable solvent. Suitable solvents include lower alkanols such as ethanol and methanol, methylene chloride, carbon tetrachloride and benzene. The reaction is generally carried out in the presence of an acid catalyst. Suitable acid catalysts include p-toluenesulfonic acid, boron trifluoride etherate, hydrogen chloride, pyridine hydrochloride and the like. The reaction is preferably carried out at room temperature although temperatures from 0° C to the boiling point of the solvent may also be employed. The product is isolated by techniques known in the art. No loss of the acetonide group is observed and the 20-keto group remains unattacked by the thioketalizing reagent due to the steric hindrance around the 20-carbonyl group.

Those compounds where $R_1$ is lower acyl, tetrahydropyranyl or lower alkyl, and $R_2$ is lower acyl can be prepared by using the appropriate ester or ether as the starting material; alternatively the ester or ether can be prepared after thioketalization by esterification and etherification methods known in the art. For example, the esters can be prepared by reaction with an acid anhydride such as acetic anhydride and the ethers can be prepared by reaction with dihydropyran, diazomethane or other known etherifying agents.

Those starting materials wherein X is fluoro, chloro, or bromo, can be prepared by techniques known in the art. A suitable procedure for preparing the starting materials is that described by Mills and Bowers.

The compounds of the present invention exhibit strong anti-inflammatory activity when tested in standard procedures using oral administration and also by topical administration. The novel compounds of this invention exhibit strong anti-inflammatory activity when administered by topical administration. The percent increase in weight of inflamed tissue dropped sharply when the steroidal thioketal was administered during the test period.

Thus the compounds of the present invention are useful in the treatment of such conditions as rheumatoid arthritis and atopic dermatitis. They may be formulated with conventional corticoid carriers in pills, tablets, capsules, etc., for oral administration. They may also be formulated in ointments, salves and the like for topical administration and in solution or suspension for injection. The compounds have been found to be effective when administered in a range from about 0.00375 to about 0.25000 mg./kg.

The anti-inflammatory activity of the halo steroidal thioketals is determined as follows:

Therapeutic Treatment of Adjuvant Arthritis in Rats

Carworth Wistar (Lewis) rats weighing approximately 200 grams are anesthetized with ether, weighed and their hind paws measured by means of a mercury displacement method. The left hind paw is injected intradermally with heat-killed *Mycobacterium tuberculosis* in white mineral oil. Measurements of body weight and paw volume are obtained on days 2, 5, 10, 15, 20 and 25. Therapeutic treatment is started on day 15.

Following the injection with *Mycobacterium tuberculosis*, a primary inflammation develops immediately in the injected paw. Secondary inflammation of the joints of the other legs and feet, nodules on the tail and red spots on the ears develop about day 10–15. The object of the test is to determine the anti-inflammatory effects of the drug treatments.

Groups of rats (five rats/group) are treated as follows: One group receives no *Mycobacterium tuberculosis* and is the negative control group. One group receives *Mycobacterium tuberculosis* but no anti-inflammatory drug and is the positive control group. Other groups receive *Mycobacterium tuberculosis* and either oral or topical test compounds or standard anti-inflammatory agents beginning on day 15 and are considered experimental groups. Experimental anti-inflammatory and standard anti-inflammatory compounds are administered either once every five days, i.e., after grading on days 15 and 20, or once/day on days 15-24.

In the topical studies a measured amount of drug is mixed into about 0.5 ml of SILASTIC* Medical Adhesive (or other appropriate vehicle) and applied to cover the left hind paw. Rats so treated are housed individually to eliminate the removal of the medication by another rat. The following, Tables 1 and 2 illustrate the anti-inflammatory potency and efficacy of the oral and topical treatments.

* Registered Trademark

TABLE 1

The anti-inflammatory effect of oral 6α,9-difluoro-pregna-1,4-diene-11β,17,21-tetrol-3,20-dione-3-ethylenedithioketal-16,17-acetonide* and fluocinolone acetonide**, administered once per day to rats with adjuvant arthritis:

| Dose (mg/kg) | Percent Inhibition of Left Hind Paw Inflammation | |
| --- | --- | --- |
| | Compound A | Compound B |
| 0.00375 | 5 | 19 |
| 0.00750 | 9 | 15 |
| 0.01500 | 43 | 32 |
| 0.03000 | 34 | 66 |
| 0.06250 | 60 | 76 |
| 0.12500 | 83 | 64 |
| 0.25000 | 95 | — |

*Compound A
** Compound B

TABLE 2

A comparison of the anti-inflammatory effects of oral and topical (in SILASTIC* Medical Adhesive) 6α,9-difluoropregna-1,4-diene-11β,16α,17,21-tetrol-3,20-dione-3-ethylenedithioketal-16,17-acetonide administered once every five days to rats with adjuvant arthritis:

| Dose (mg/kg/5 days) | Percent Inhibition of Left Hind Paw Inflammation | |
| --- | --- | --- |
| | Oral | Topical |
| 0.075 | 14.7 | — |
| 0.150 | 15.3 | — |
| 0.300 | 18.1 | 31.1 |
| 0.625 | 29.0 | 52.6 |
| 1.250 | 35.0 | 57.5 |
| 2.500 | 44.3 | 64.5 |

*Registered Trademark

EXAMPLE 1

6α,9-Difluoro-11β,16α,17,21-tetrahydroxypregna-1,4-diene-3,20-dione-16,17-acetonide-3-ethylenedithioketal One g. of 6α,9-difluoro-11β,16α,17,21-tetrahydroxypregna-1,4-diene-3,20-dione-16,17-acetonide, 0.5 ml. of ethanedithiol, and 0.2 g. of paratoluenesulfonic acid are stirred together in 20 ml. of methanol at 25° C. After about 15 minutes, solution is complete.

The solution is then allowed to stand overnight (about 18 hours). Water is added until the solution becomes cloudy; 0.5 ml. of ammonium hydroxide is then added, followed by the addition of water to a final volume of 50 ml. The precipitate which forms is collected by filtration. The filtrate is steam distilled to remove methanol and ethanedithiol, after which it is extracted with methylene chloride. The extracts are added to the solid.

The combined products from the reaction of 4 g. of the steroid are charged onto 150 g. of chromatographic grade silicic acid in a column. Elution with 10 percent ethyl acetate in benzene yields 3.4 g. of 6α,9-difluoro-11β,16α, 17,21-tetrahydroxypregna-1,4-diene-3,20-dione-16,17-acetonide-3-ethylenedithioketal. An analytically pure sample is obtained upon recrystallization from methanol.

| Rotation: | | 103° |
| --- | --- | --- |
| M. P.: | | 173-177° |
| Elemental Analysis: | | |
| | Theoretical | Found |
| C | 59.07 | 59.23 |
| H | 6.48 | 6.87 |

When in the above procedure 6α,9-dibromo-11β,16α, 17,21-tetrahydroxypregna-1,4-diene-3,20-dione-16,17-acetonide-3-ethylenedithioketal is employed instead of the difluoro compound, the corresponding dibromo thioketal is obtained.

EXAMPLE II

6α,9-Difluoro-11β,16α,17,21-tetrahydroxypregna-1,4-diene-3,20-dione-16,17-acetonide-3-propylenedithioketal To a solution of 6α,9-difluoro-16α-hydroxyprednisolone-16,17-acetonide (0.5 g.; 0.00108 moles) in 25 ml. of methanol is added 0.8 ml. of propanedithiol and 0.8 ml. of freshly distilled boron trifluoride etherate. The reaction mixture is allowed to stand for 45 minutes, after which the mixture is poured into 100 ml. of water. The aqueous mixture is then extracted several times with ether. Upon removal of the solvent, 0.25 g. of a crude solid material is obtained. After two recrystallizations from ether-hexane and one recrystallization from benzene-hexane, 0.1 g. of 6α,9-difluoro-11β,16β,17,21-tetrahydroxypregna-1,4-diene-3,20-dione-16,17-acetonide-3-propylenedithioketal is obtained as a colorless solid, m.p. 195°-196° C.

Anal. Calculated for $C_{27}H_{36}F_2O_5S_2$: C, 59.76; H, 6.76, Found: C, 59.72; H, 6.88.

When in the above procedure butanedithiol or pentanedithiol is employed in place of propanedithiol, 6α,9-difluoro-11β,16α,17,21-tetrahydroxypregna-1,4-diene-3,20-dione-16,17-acetonide-3-butylenedithioketal or 6α,9-difluoro 11β,16α,17,21-tetrahydroxypregna-1,4-diene-3,20-dione-16,17-acetonide-3-pentylenedithioketal is obtained.

When in the above procedure 6α,9-dichloro-11β,16α, 17,21-tetrahydroxypregna-1,4-diene-3,20-dione-16,17-acetonide-3-ethylenedithioketal is employed in place of the difluoro acetonide, the corresponding dichloro dithioketal is obtained.

EXAMPLE III

6α,9-Difluoro-6α-hydroxyprednisolone-16, 17-acetonide-3-ethylene hemithioketal

To a solution of 6α,9-difluoro-16α-hydroxyprednisolone 16,17-acetonide (0.5 g.; 0.00108 moles) in 25 ml. of methanol is added 0.6 ml. of 2-mercaptoethanol, and 0.6 ml. of freshly distilled boron trifluoride-etherate.

The reaction mixture is allowed to stand for 1 hour at room temperature, and then poured into 100 ml. of ice-water. The aqueous slurry is extracted several times with ether. Upon removal of the solvent 0.22 g. of colorless crystals identified as starting steroids is obtained. The aqueous portion is concentrated to dryness in vacuo and the residue washed well with ether. Concentration of the ether washes yields 0.11 g. of 3-ethylene hemithioketal, m.p. 135°–140° C. Vigorous drying (over refluxing toluene for 2 days) provides a sample melting at 145°–150° C.

Anal. Calculated for $C_{26}H_{34}F_2O_6S\cdot H_2O$: C, 58.86; H, 6.78, Found: C, 58.46; H, 6.61, When in the above procedure 2-mercaptopropanol and 2-mercaptobutanol are employed in place of 2-mercaptoethanol, 6α,9-difluoro-6α-hydroxyprednisolone-16,17-acetonide-3-propylene hemithioketal and 6α,9-difluoro-6α-hydroxyprednisolone-16,17-acetonide-3-(2'-ethyl ethylene) hemithioketal, respectively, are obtained.

EXAMPLE IV

6α,9-Difluoropregna-1,4-diene-11β,16α,17,21-tetrol-3,20-dione-3-ethylenedithioketal-16,17-acetonide-21-tetrahydropyranyl ether A solution of 20 mg. of 6α,9-difluoro-11β,16α,17,21-tetrahydroxypregna-1,4-diene-3,20-dione-16,17-acetonide-3-ethylenedithioketal in 1 ml. of dihydropyran and one drop of ethereal hydrogen chloride is allowed to stand at room temperature for 3 days. Two drops of aqueous ammonium hydroxide are added, and the reaction mixture is evaporated to dryness under a stream of nitrogen. The solid residue is extracted with methylene chloride, and the solution is dried by filtration through anhydrous magnesium sulfate. The filtrate is streaked on a neutral silicic acid 250 micron thin layer chromatographic plate, and the plate is developed with ethyl acetate-cyclohexane.

The uppermost component is removed from the plate and the steroid is eluted from the silicic acid with acetone, methylene chloride. The solution is evaporated to dryness to yield the title compound, and a sample is subjected to mass spectroscopy and infrared absorbtion spectroscopy. The infrared absorbtion at 2.8–3.0 microns is only half as strong as for the corresponding diol starting material, indicating one hydroxyl group has been derivatized.

When in the above procedure diazomethane is employed in place of dihydropyran and in the absence of hydrogen chloride, the corresponding methyl ether is obtained.

EXAMPLE V

6α,9-Difluoropregna-1,4-diene-11β,16α,17,21-tetrol-3,20-dione-3-ethylenedithioketal-16,17-acetonide-11,21-diacetate To 100 mg. of 6α,9-difluoro-11β,16α,17,21-tetrahydroxypregna-1,4-diene-3,20-dione-16,17-acetonide-3-ethylene dithioketal is added 3 ml. of pyridine and 3 ml. of acetic anhydride. After stirring at room temperature overnight the resulting solution is concentrated to dryness. Crystallization of the residue from methanol affords 6α,9-difluoropregna-1,4-diene-11β, 16α,17,21-tetrol-3,20-dione-3-ethylenedithioketal-16,17-acetonide-11,21-diacetate, m.p. 188°–189° C.

Anal. Calculated for $C_{30}H_{38}F_2O_7S_2$: C, 58.80; H, 6.25, Found: C, 58.51; H, 6.22, When in the above procedure propionic anhydride or butyric anhydride is employed in place of acetic anhydride, 6α,9-difluoropregna-1,4-diene-11β,16α,17,21-tetrol-3,20-dione-3-ethylenedithioketal-16,17-acetonide-11,21-dipropionate and 6α,9-difluoropregna-1,4-diene-11β,16α, 17,21-tetrol-3,20-dione-3-ethylenedithioketal-16,17-acetonide-11,21-dibutyrate respectively are obtained.

When in the above procedure valeric anhydride is employed in place of acetic anhydride, 6α,9-difluoropregna-1,4-diene-11β,16α,17,21-tetrol-3,20-dione-3-ethylenedithioketal-16,17-acetonide-11,21-divalerate is obtained.

B.

6α,9-Difluoropregna-1,4-diene-11β,16α,17,21-tetrol-3,20-dione-3-ethylendithioketal-16, 17-acetonide-21-acetate The mother liquor is chromatographed on a thin-layer chromatographic plate developed with 30% ethyl acetate-70% cyclohexane. The area corresponding to 6α,9-difluoropregna-1,4-diene-22β,16α,17,21 -tetrol-3,20-dione-3-ethylenedithioketal-16,17-acetonide-21-acetate is scraped off and the 6α,9-difluoropregna-1,4-diene-11β,16α, 17,21-tetrol-3,20-dione-3-ethylenedithioketal-16,17-acetonide-21-acetate is eluted from the silicic acid with 50% methanol-50% methylene chloride. The solvents are evaporated and the solid remaining is crystallized from methanol to yield a crystalline product, m.p. 218°–220° C.

Anal. Calculated for $C_{28}H_{30}F_2O_6S_2$: C, 58.92; H, 6.36, Found: C, 58.85; H, 6.35.

When in the above procedure propionic anhydride, butyric anhydride or valeric anhydride is employed in place of acetic anhydride, 6α,9-difluoropregna-1,4-diene-11β,16α, 17,21-tetrol-3,20-dione-3-ethylenedithioketal-16,17-acetonide-21-propionate; 6α,9-difluoropregna-1,4-diene-11β,16α,17, 21-tetrol-3,20-dione-3-ethylenedithioketal-16,17-acetonide-21-butyrate and 6α,9-difluoropregna-1,4-diene-11β,16α,17-21-tetrol-3,20-dione-3-ethylenedithioketal-16,17-acetonide-21-valerate respectively are obtained.

While the invention has been described and illustrated with reference to certain preferred embodiments thereof, those skilled in the art will appreciate that various modifications, changes, omissions and substitutions can be made without departing from the spirit of the invention. It is intended, therefore, that the invention be limited only by the scope of the following claims. 9

What is claimed is:

1. A method of treating inflammation which comprises administering an effective amount of a compound of the formula:

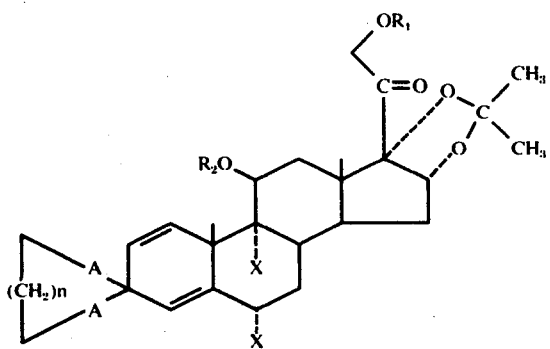

in a pharmaceutically acceptable carrier, wherein $R_1$ is hydrogen, lower acyl having 2–5 carbon atoms, tetrahydropyranyl or lower alkyl; $R_2$ is hydrogen or lower acyl having 2–5 carbon atoms; A is oxygen or sulfur provided that at least one of A is sulfur; $x$ is fluoro, chloro or bromo, and $n$ is an integer from 0–3.

2. The method of claim 1 wherein $R_1$ and $R_2$ are hydrogen, $x$ is fluoro and A is sulfur.

3. The method of claim 1 wherein $R_1$ and $R_2$ are hydrogen or acyl, $x$ is fluoro and A is sulfur.

4. The method of claim 1 wherein $R_1$ and $R_2$ are hydrogen or acyl, $x$ is fluoro and A is sulfur.

5. The method of claim 1 wherein $x$ is fluoro.

6. The method of claim 1 wherein A is sulfur.

7. The method of claim 1 wherein A is oxygen.

8. The method of claim 1 wherein the compound is 6α,9-difluoro-11β,16α,17,21-tetrahydroxypregna-1,4-diene-3,20-dione-16,17-acetonide-3-ethylenedithioketal.

9. The method of claim 1 wherein the compound is 6α,9-difluoro-11β,16α,17,21-tetrahydroxypregna-1,4-diene-3,20 dione-16,17-acetonide-3-propylenedithioketal.

10. The method of claim 1 wherein the compound is 3-ethylene hemithioketal.

* * * * *

UNITED STATES PATENT OFFICE
CERTIFICATE OF CORRECTION

Patent No. 4,014,999         Dated March 29, 1977

Inventor(s) Robert A. Mallory et al.

It is certified that error appears in the above-identified patent and that said Letters Patent are hereby corrected as shown below:

In Column 1, line 37, there should be a colon after the word "formula".

In Column 2, line 22, after the words "Mills and Bowers" the following was omitted: --- [J. S. Mills, A. Bowers, Carl Djerassi and H. J. Ringold J.A.C.S., 82, 3399 (1960)] ---.

In Column 3, line 17 should read: --- pregna-1,4-diene-11β,16α,17,21-tetrol-3,20-dione-3- ---.

In Column 4, line 43, the word "16β" should read --- 16α ---.

In Column 5, line 44, the word "spectroscopY" should read --- spectroscopy ---.

In Column 5, approximately line 53, there should be a subheading "A." after "Example V".

In Column 6, line 21, the word "3-ethylendithioketal" should read --- 3-ethylenedithioketal ---.

UNITED STATES PATENT OFFICE
CERTIFICATE OF CORRECTION

Patent No. 4,014,999  Dated March 29, 1977

Inventor(s) Robert A. Mallory et al.

It is certified that error appears in the above-identified patent and that said Letters Patent are hereby corrected as shown below:

In Column 6, line 27, the word "22β" should read --- 11β ---.

In Column 8, line 7, in Claim 4, the word "acyl" should read --- acetyl ---.

Signed and Sealed this

Twenty-first Day of June 1977

[SEAL]

Attest:

RUTH C. MASON
Attesting Officer

C. MARSHALL DANN
Commissioner of Patents and Trademarks